US012144708B2

United States Patent
Comparone et al.

(10) Patent No.: US 12,144,708 B2
(45) Date of Patent: Nov. 19, 2024

(54) ABSORBENT LIQUID MEASUREMENT ARTICLE

(71) Applicant: Hill-Rom Services, Inc., Batesville, IN (US)

(72) Inventors: Nicholas Comparone, Batesville, IN (US); Edward Koors, Indianapolis, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 1099 days.

(21) Appl. No.: 17/010,142

(22) Filed: Sep. 2, 2020

(65) Prior Publication Data

US 2021/0077311 A1 Mar. 18, 2021

Related U.S. Application Data

(60) Provisional application No. 62/901,410, filed on Sep. 17, 2019.

(51) Int. Cl.
*A61F 13/42* (2006.01)
*G01N 33/493* (2006.01)
*A61F 13/537* (2006.01)
*A61F 13/84* (2006.01)

(52) U.S. Cl.
CPC ........... *A61F 13/42* (2013.01); *G01N 33/493* (2013.01); *A61F 2013/424* (2013.01); *A61F 13/53713* (2013.01); *A61F 2013/53765* (2013.01); *A61F 2013/8473* (2013.01); *A61F 2013/8479* (2013.01)

(58) Field of Classification Search
CPC ................ A61F 13/42; A61F 2013/422; A61F 2013/429; A61F 13/00055; A61F 13/53713; A61F 2013/53765; A61F 2013/8479; G01N 33/493
USPC ............................................................ 4/661
See application file for complete search history.

(56) References Cited

U.S. PATENT DOCUMENTS

| | | | |
|---|---|---|---|
| 6,284,492 B1 | 9/2001 | Donson et al. | |
| 7,241,627 B2 * | 7/2007 | Wilhelm | A61F 13/42 422/50 |
| 8,053,625 B2 * | 11/2011 | Nhan | A61F 13/42 600/362 |
| 10,159,607 B2 | 12/2018 | Monson et al. | |
| 10,349,881 B1 | 7/2019 | Monson et al. | |
| 2003/0078553 A1 | 4/2003 | Wada et al. | |
| 2012/0157948 A1 * | 6/2012 | Nhan | A61F 13/42 604/361 |
| 2018/0021184 A1 * | 1/2018 | Monson | H01Q 9/0457 340/573.5 |
| 2022/0047430 A1 * | 2/2022 | Luck | A61F 13/51496 |

FOREIGN PATENT DOCUMENTS

JP 2019080671 A 5/2019

* cited by examiner

*Primary Examiner* — Susan S Su
(74) *Attorney, Agent, or Firm* — Dinsmore & Shohl LLP

(57) ABSTRACT

A liquid measurement article includes an absorbent wicking layer and a marking cluster having at least one mark whose location on the article is calibrated to correspond to a particular quantity of liquid having been deposited on the article at a liquid receiving site thereof and having wicked toward the mark. A label associated with at least one of the marks indicates the particular quantity.

26 Claims, 16 Drawing Sheets

ABSORBENT LIQUID MEASUREMENT ARTICLE

CROSS-REFERENCE TO RELATED APPLICATIONS

The present specification claims the benefit of U.S. Provisional Application Ser. No. 62/901,410 entitled "Absorbent Liquid Measurement Article" and filed Sep. 17, 2019, the contents of which is incorporated herein in its entirety.

TECHNICAL FIELD

The subject matter described herein relates to an absorbent article having a liquid quantity measurement capability. In one example the article is embodied as an incontinence pad with calibrated markings that reveal the liquid volume of an incontinence episode.

BACKGROUND

In certain health care settings, for example a hospital intensive care unit (ICU), a patient may be catheterized due to their medical condition and in order to measure the patient's urinary output, which can be clinically significant. Unfortunately, the use of a catheter can cause a number of complications such as infection of the patient's urinary tract. Catheter related complications can be avoided by using an incontinence pad instead of a catheter to collect the patient's urine. However incontinence pads do not provide any capability to monitor the patient's urine output. This lack of urine output monitoring capability is a barrier to the use of incontinence pads in ICU settings, despite their benefit in preventing catheter related complications.

Therefore, it would be beneficial to provide an incontinence pad that can indicate the quantity of urine deposited on the pad. Such a pad could be used instead of a catheter, avoiding the potential complications of catheter use while nevertheless providing clinically useful information about the patient's urinary output.

SUMMARY

A liquid measurement article includes an absorbent wicking layer and a marking cluster. The marking cluster includes at least one mark calibrated to correspond to a particular quantity of liquid which has been deposited on the article at a liquid receiving site thereof and which has wicked toward the mark. A label is associated with one or more of the marks. The label indicates the particular quantity of deposited liquid.

BRIEF DESCRIPTION OF THE DRAWINGS

The foregoing and other features of the various embodiments of the liquid measurement article described herein will become more apparent from the following detailed description and the accompanying drawings in which.

DETAILED DESCRIPTION

Figure 1:
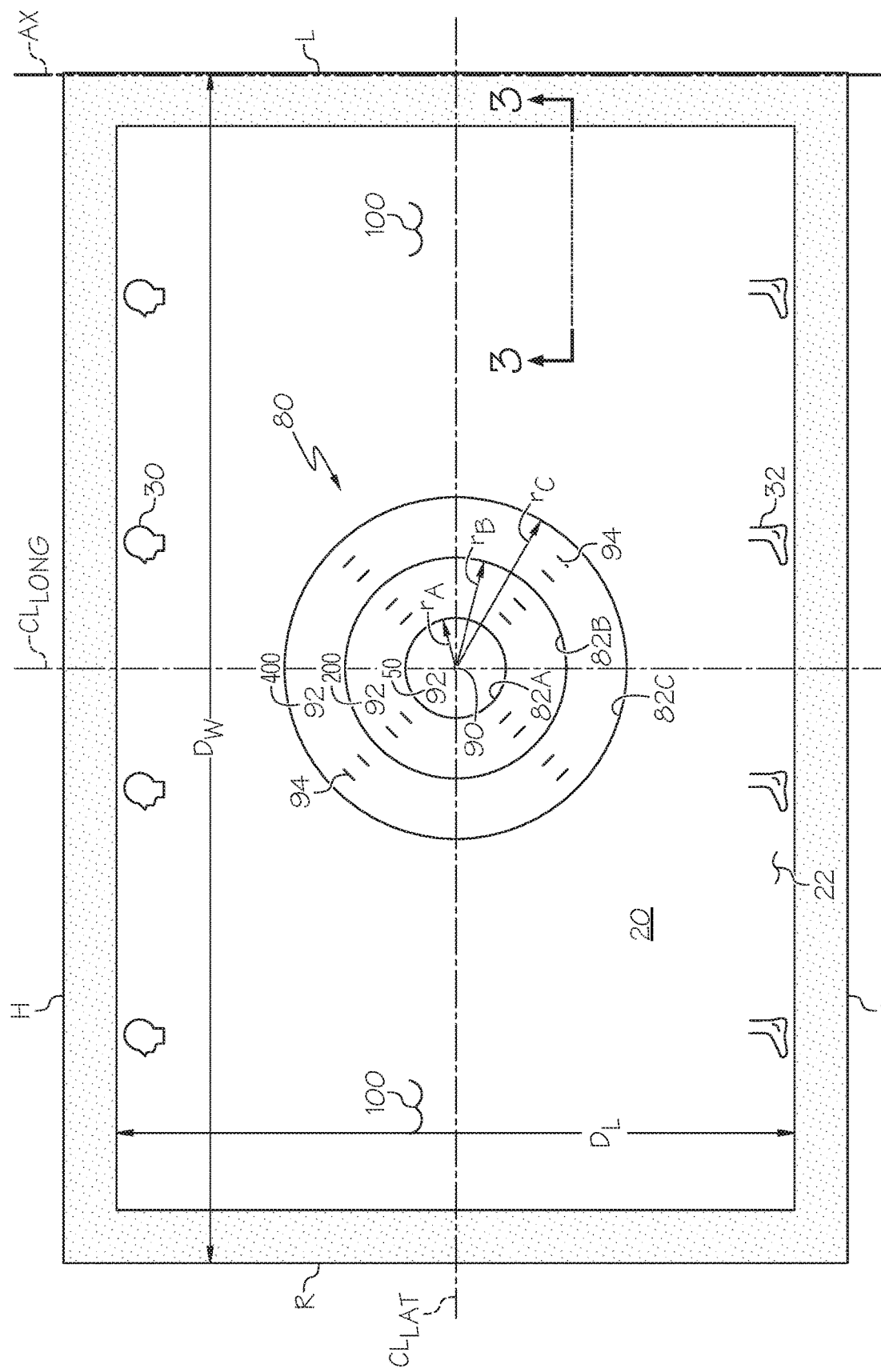
FIG. 1 is a plan view of the patient side of an absorbent liquid measurement article, embodied as an incontinence pad.

The liquid measurement articles described herein may comprise one or more of the features recited in the appended claims and/or one or more of the following features or combinations thereof.

In this specification and drawings, features similar to or the same as features already described may be identified by reference characters or numerals which are the same as or similar to those previously used. Similar elements may be identified by a common reference character or numeral, with suffixes being used to refer to specific occurrences of the element.

The following are incorporated herein by reference: U.S. Pat. No. 10,159,607 entitled "Incontinence Detection Apparatus" issued on Jul. 16, 2019; and U.S. Pat. No. 10,349,881 entitled "Incontinence Detection System", issued on Dec. 25, 2018.

Figure 2:
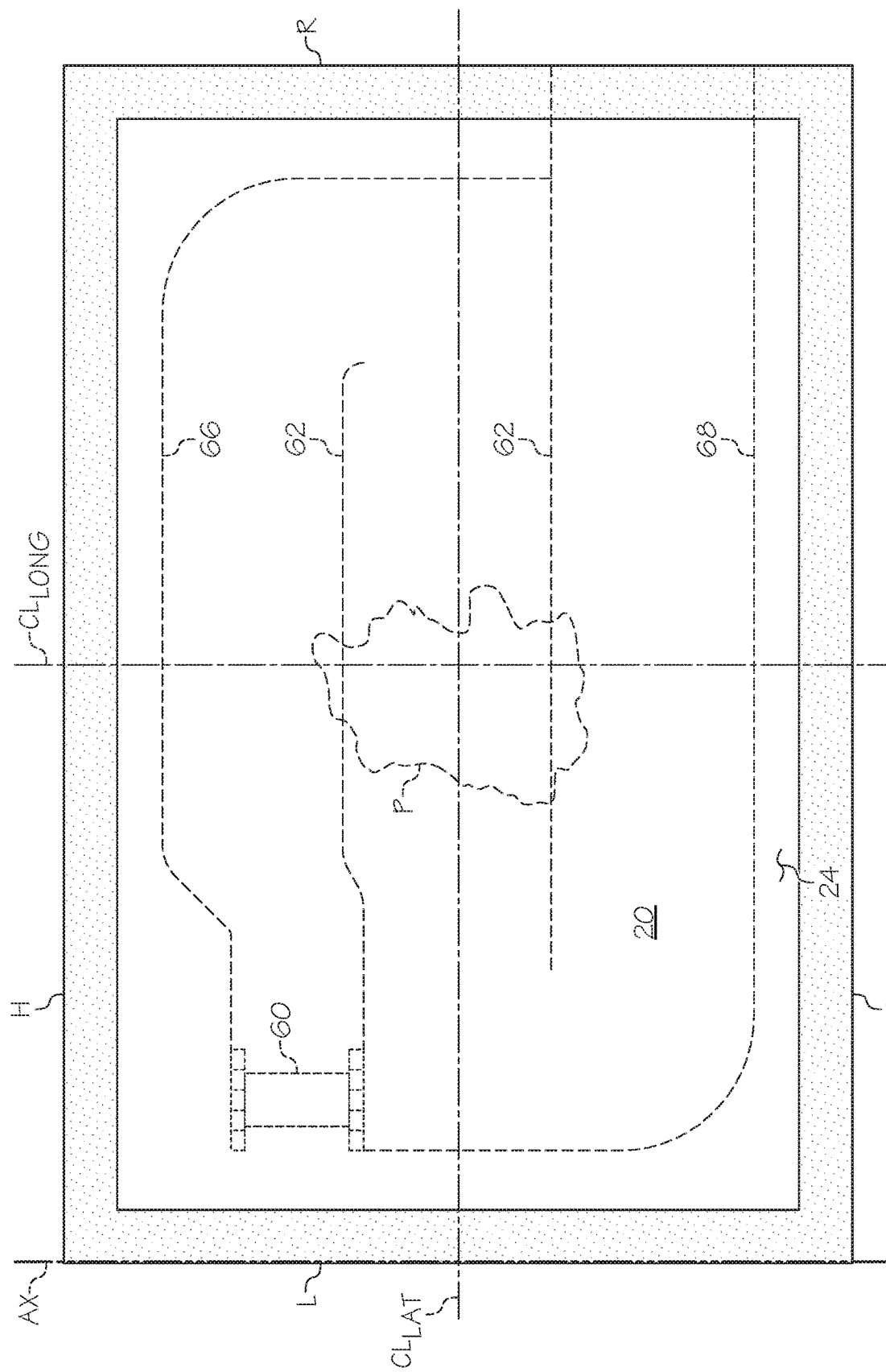
FIG. 2 is a plan view of the opposite or mattress side of the pad of FIG. 1.
Figure 3:
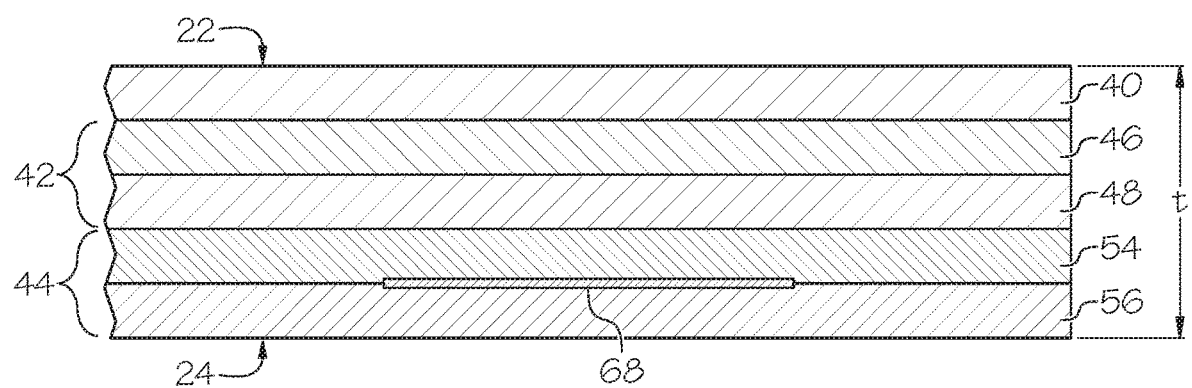
FIG. 3 is a schematic cross section along 3-3 of FIG. 1.

FIG. 1 is a plan view of a liquid measurement article embodied as an incontinence pad 20 and showing the patient or person side or top side 22 of the pad. FIG. 2 is a plan view of the incontinence pad of FIG. 1 flipped 180 degrees about axis AX to show the mattress side or bottom side 24 of the pad. The pad is placed on a mattress (which is supported by a bed frame, not illustrated) with the patient side "up" facing the patient and with the mattress side "down", facing the mattress. FIG. 3 is a cross sectional elevation view taken at 3-3 of FIG. 1.

The illustrated pad has a rectangular planform having a longitudinal dimension or length $D_L$ of about 76 cm, a lateral dimension or width $D_W$ of about 89 cm, and an uncompressed thickness t on the order of about of about one millimeter at its thickest part. The term "rectangular" and its variants include a square. Nonrectangular planforms may also be satisfactory.

FIGS. 1-2 and other drawings show longitudinally and laterally extending centerlines $CL_{LONG}$, $CL_{LAT}$, however these are shown for reference only and are not physically present on the actual article.

Unlike some articles found in the literature, the article described herein is not adapted to conform to the human crotch, as is the case for the articles of Japanese Patent JP 2019 080 671 and US Patent Publication US 2003/007 8553, or to any other human surface anatomy feature. Instead, the article is nonwearable, which simply means not wearable. A wearable article is one that is adapted to be or to simulate an item of clothing. Wearability may also be signaled by the article having a shape or contour that approximately conforms to the shape of the human body or portion thereof. Wearability may also be signaled by the article being adapted to enclose or adhere to a portion of the human body, for example the way a bandage might encircle an injury on a person's arm or a bandaid might adhere to a person's skin over top of a cut. Wearability may also be indicated if the article is designed to be held against a human body by a piece of clothing, the way that a wearable incontinence pad might be designed to be held against a person's body by his underwear, but without the use of adhesive. By contrast, the article described herein is adapted to be placed between a patient and the mattress of a bed so that the patient lies on the article.

The article described herein is also not adapted to be color sensitive in response to the constituents of a liquid deposited thereon, as is the case with the confidence building incontinence pad of U.S. Pat. No. 6,284,492. Instead, pad 20 is color stable in response to the deposition of liquid thereon and therefore is less complicated than the pad of the '492 patent. Color stable means that pad 20 does not include materials intended by design to react chemically with constituents of the urine by changing to a color indicative of the specific constituent. The possibility that the urine will stain pad 20 does not defeat its property of being color stable because staining is not considered herein to be a chemical reaction, nor does staining reveal anything about the composition or constituents of the urine.

Pad 20 has a head end H, which is the longitudinal end intended to be placed on the mattress closer to the patient's head, and a foot end F which is the longitudinal end intended to be placed on the mattress closer to the patient's feet. A head emblem 30 and a foot emblem 32 are visible on the patient side of the pad to guide a caregiver as to the correct orientation of the pad relative to the patient. The pad also has a left side L and a right side R where left and right are from the perspective of a supine patient lying on the pad.

Referring to FIG. 3, the pad is comprised of a liquid permeable top layer 40, a core 42 beneath the top layer, and a back sheet 44. The core is comprised of an absorbent wicking layer 46 and a barrier layer 48 beneath the wicking layer. Wicking layer 46 and barrier layer 48 may be thought of as sublayers of core 42. Back sheet 44 is comprised of a liquid impermeable backing layer or backing 54 and a nonwoven strengthening layer 56 beneath the backing 54. Backing 54 and strengthening layer 56 may be thought of as sublayers of back sheet 44. The term "beneath" describes the vertical relationship amongst the various layers such that a first layer which is beneath a second layer is vertically lower than the second layer when the pad is laid flat with its patient side 22 (i.e., the top side 22) facing up, toward the patient, and its mattress side 24 (i.e., the bottom side 24) facing down, toward the mattress.

Absorbent wicking layer 46 is made of wood pulp and a super absorbent polymer. The absorbent wicking layer absorbs liquid which has been deposited on the pad and has soaked through the top layer (e.g. urine resulting from an incontinence episode) and wicks the liquid away from its place of deposition. As used herein, "place of deposition" is a general term referring to any place on the pad where the liquid happens to have been deposited. When a particular place (or places) of deposition has been envisioned by the designers of the pad, as is the case with the pad disclosed in this specification and drawings, the place of deposition is referred to as a liquid receiving site. The wicking layer traps some but not all of the liquid. The remainder of the liquid is released to backing 54. The amount of liquid released is regulated by the design of barrier layer 48.

This specification uses "wick", "wicking" and related terms as terms of convenience to describe the passive migration of liquid through the absorbent layer away from the receiving site. However neither the specification nor the claims are limited to any particular mechanism of or theory of liquid transport. The transport of liquid is referred to as "passive" because it is a naturally occurring phenomenon rather than a transport driven by a pump, suction device or other powered device.

The top layer and strengthening layer define pad dimensions $D_L$ and $D_W$. The wicking layer, barrier layer and backing layer extend longitudinally and laterally less than the full longitudinal and lateral dimensions $D_L$, $D_W$ of the pad.

Referring to FIGS. 2 and 3, the illustrated pad includes an RFID tag 60 and an associated electrical trace assembly 62. The trace assembly and RFID tag are embedded in the pad but are nevertheless visible from the bottom side of the pad. The electrical trace assembly includes a first trace 66 extending from a first terminal of the tag and a second trace 68 extending from a second terminal of the tag. The traces define an open circuit. One or more RFID readers, not illustrated, may be installed on the bed frame to read the tag. The head and foot emblems 30, 32 on the patient side of the pad indicate the orientation of the pad that will result in best communication between the RFID tag 60 and the RFID reader or readers.

In operation, urine deposited on top layer 40 soaks through to the absorbent wicking layer. The wicking layer wicks urine away from the site of deposition. The barrier layer allows penetration of some of the urine to the back sheet. The absorbent layer and the barrier layer are designed to promote closure of the RFID circuit in response to deposition of a threshold amount of liquid on the pad. In other words there is some threshold quantity of urine which will spread out far enough in the backing layer to bridge between the first and second traces 66, 68, as seen in the example patch of urine P in FIG. 2. (The outline of the urine patch is illustrated with a dashed line because the urine does not ordinarily soak through strengthening layer 56.) The electrical conductivity of the urine closes the circuit. The RFID tag reports the closure to an RFID reader so that knowledge of the incontinence episode can be communicated to a caregiver. The RFID enabled moisture detection and reporting system just described is useful either standing alone or in conjunction with the liquid measurement article described in this specification. However the liquid measurement article described herein is useful on its own and therefore need not include the RFID system. Examples of RFID based incontinence detection systems are described in U.S. Pat. Nos. 10,159,607 and 10,349,881.

Continuing to refer to FIGS. 1-3, the liquid absorbent article is in the form of a thin sheet, i.e. its length $D_L$ and width $D_W$ are both considerably larger than its thickness t. The pad is essentially planar. As used herein "planar" means that the article, when laid out on a flat surface such as a tabletop, or a substantially flat surface such as a mattress, is itself substantially flat and has a thickness far smaller than either its lateral dimension or its longitudinal dimension. The possibility that the flatness may be distorted when the article is placed on a soft surface, such as a mattress, or when the article is deployed between a person and a mattress, does not defeat its property of being planar.

Referring to FIG. 1, the incontinence pad embodiment of the article includes a marking cluster 80 having at least one mark 82. The illustrated marking cluster is present on top layer 40 but could instead be placed on any layer provided it is visible to a person from the outside of the pad. In the illustrated embodiment the pad includes three marks. The marks are concentric circles, 82A, 82B, 82C all centered on and circumscribing a liquid receiving site 90. The marks have respective radii of $r_A$, $r_B$, and $r_C$. The location of each mark on the article is calibrated to correspond to a particular quantity of liquid having been deposited on the article at the liquid receiving site 90 and having wicked toward the mark. A label 92 associated with at least one of the marks indicates the particular quantity of liquid, for example the volume markings (milliliters) shown on the drawing. In most of the drawings the label is not illustrated in order to avoid undue clutter on the drawing. The embodiment of FIG. 1 also shows inter-circle graduations 94 to assist a user in interpolating between the circles.

Figure 4:
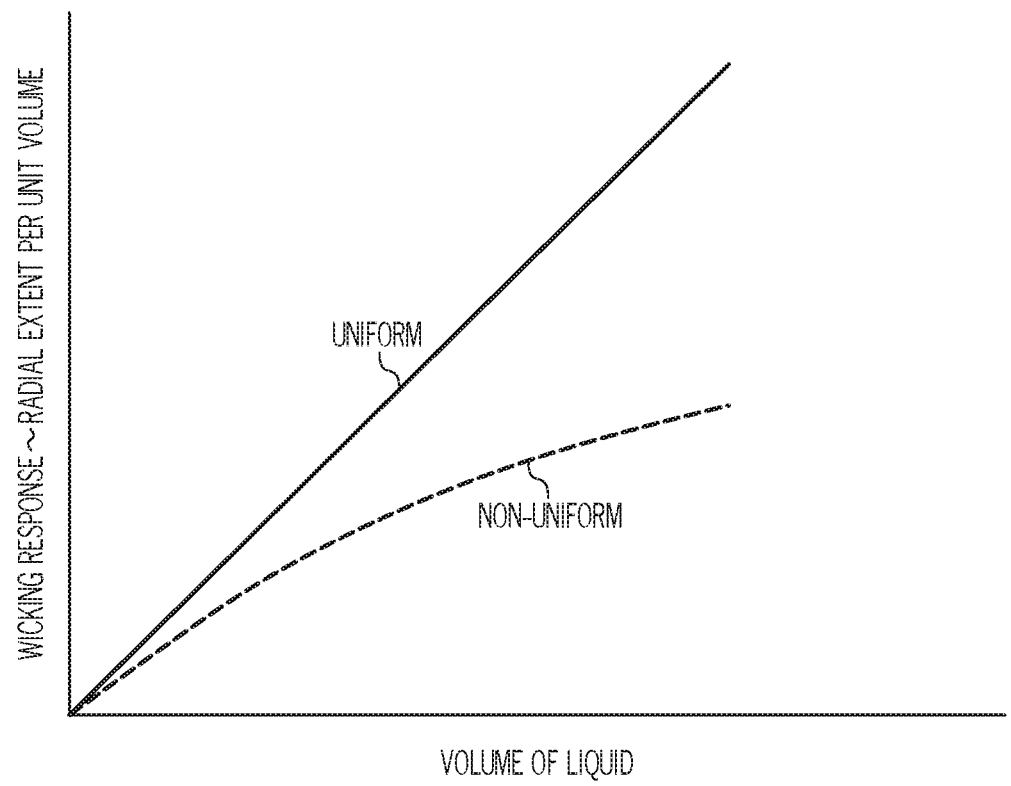
FIG. 4 is a graph showing meanings of uniform and nonuniform wicking response of an absorbent wicking layer of the pad of FIGS. 1-3.

As illustrated, $r_B$ and $r_C$ are integral multiples (2 and 3) of $r_A$. Other relationships may be at least as satisfactory, for example radii that define equal incremental areas A ($A_{82A}=A_{82B}-A_{82A}=A_{82C}-A_{82B}-A_{82A}$). Another example is radii that define equal incremental liquid volumes V wicked between liquid receiving site 90 and circle 82A, wicked between circles 82A and 82B after the liquid has wicked to circle 82A, and wicked between circles 82B and 82C after the liquid has wicked to circle 82B. The actual location of the marks will depend on the wicking response of absorbent wicking layer 46, where wicking response means the radial extent of wicking per volume of liquid (FIG. 4). Wicking response can also be expressed in terms of the lateral extent of wicking per volume of liquid in combination with the longitudinal extent of wicking per volume of liquid. In one embodiment the wicking response is radially uniform.

Before proceeding it may be helpful to elaborate on the concept of a liquid receiving site. As noted above, a liquid receiving site is a particular place (or places) of liquid deposition that has been envisioned by the designers of the pad. The deposition of urine by an incontinent patient will, of course, not be a precise point as indicated by reference numeral 90. Instead the deposition of liquid will be spatially distributed over some area of the pad, e.g. patch P of FIG. 2. Precise point 90 is therefore a useful idealization of the liquid receiving site, for example the approximated middle of the area where the designer envisions that the liquid (urine) will be deposited when the pad is properly positioned under a patient. The designer can use the idealized liquid receiving site 90 as a datum when specifying the actual positioning of the marks on the pad. The datum may be at the center of the pad as is shown in FIG. 1, or it may be off-center.

The embodiment of FIG. 1 shows a pair of indexing marks 100 for assisting a caregiver in positioning the pad longitudinally under a patient so that the actual site of urine deposition will approximate the liquid receiving site envisioned by the designer. The illustrated indexing mark has a shape which is suggestive of a person's gluteal sulcus, indicating that the pad should be placed under the patient so that mark 100 is longitudinally aligned with the patient's gluteal sulcus.

A marking cluster 80 is not necessarily comprised of two or more marks as in FIG. 1, but may include only a single mark, if desired. The single mark cluster may or may not have a label 92. A nonlabelled single mark may be useful if it is desired to merely determine if the patient's urine output has or has not exceeded an amount corresponding to the mark, although in that case it may be desirable to place the amount marking elsewhere on the pad or on its packaging. A labeled single mark may be similarly useful, but with the additional advantage of having the label conspicuous and close to the mark.

Figure 5:
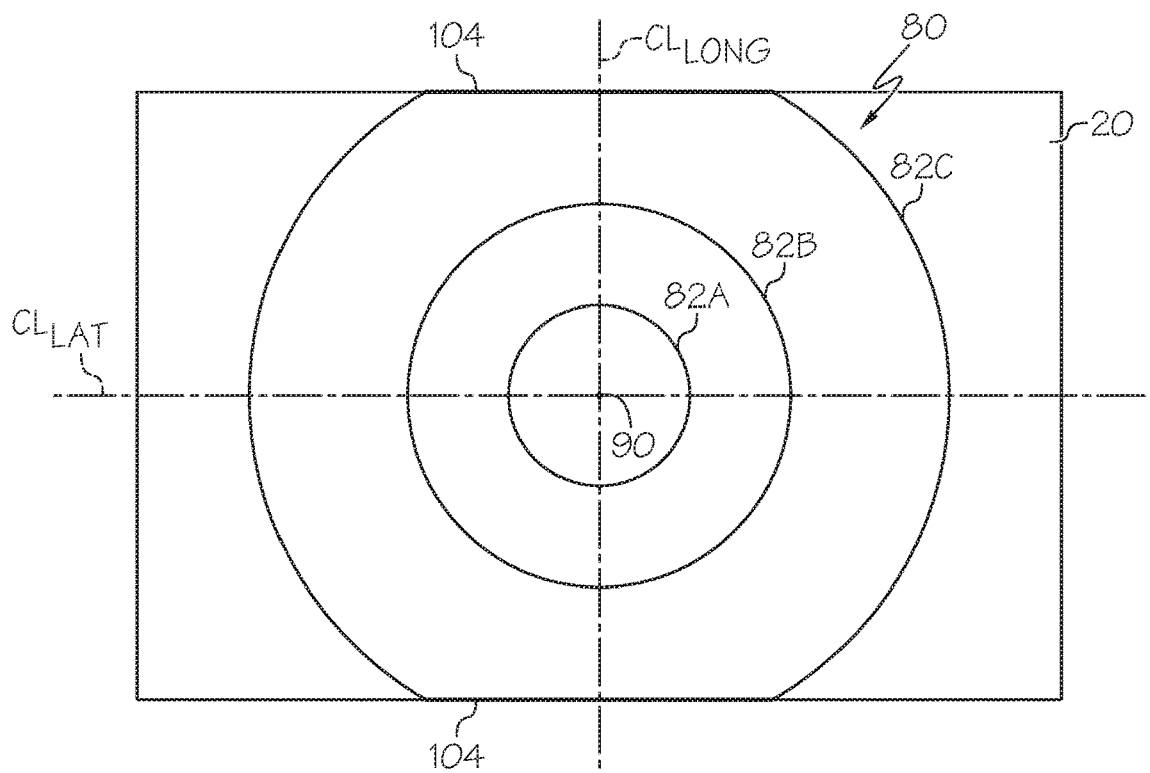
FIG. 5 is a schematic plan view of the patient side of an incontinence pad illustrating a variation of the concept of a "closed figure"
Figure 6:
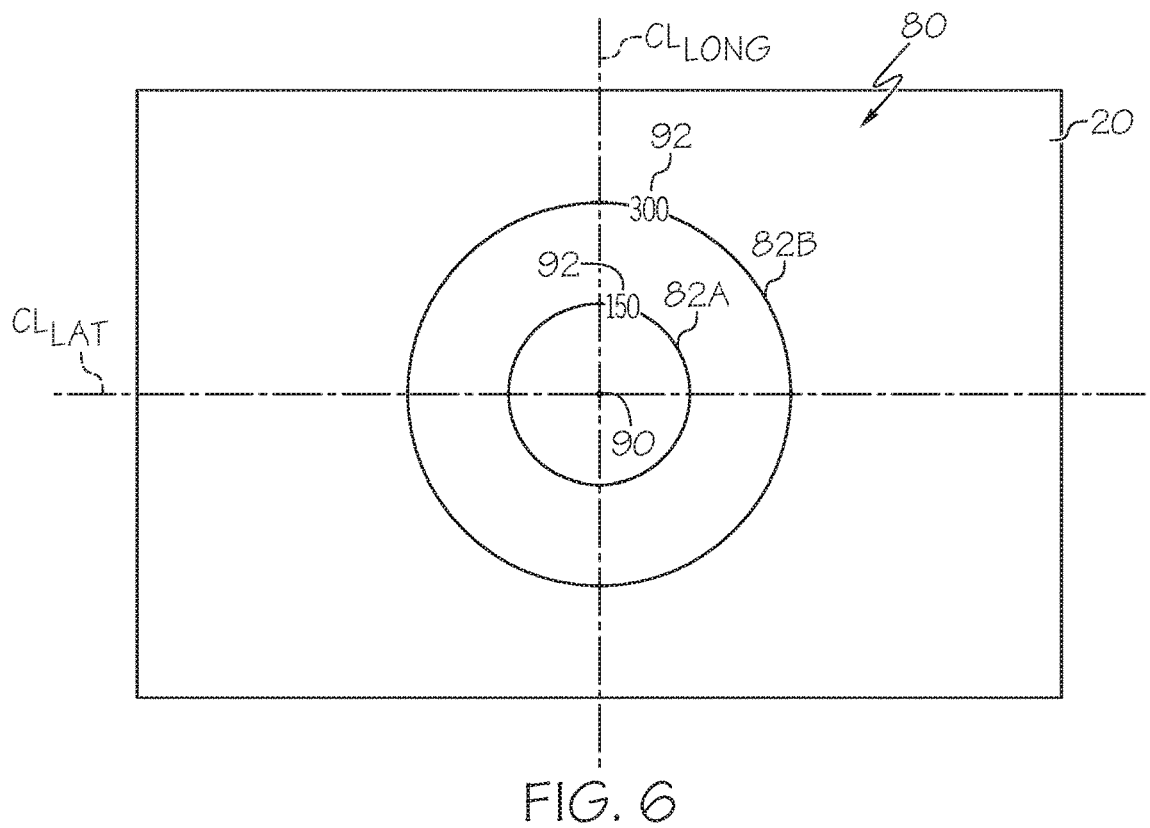
FIG. 6 is a schematic plan view of the patient side of an incontinence pad illustrating a variation of the concept of a "closed figure"
Figure 7:
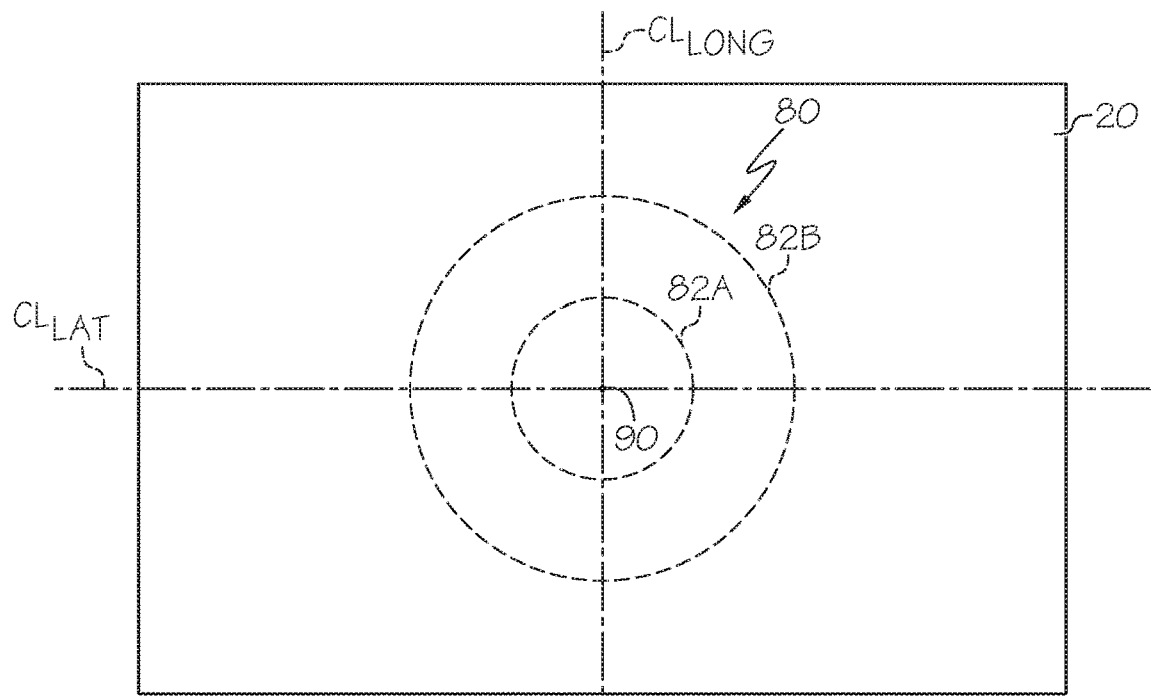
FIG. 7 is a schematic plan view of the patient side of an incontinence pad illustrating a variation of the concept of a "closed figure"
Figure 8:
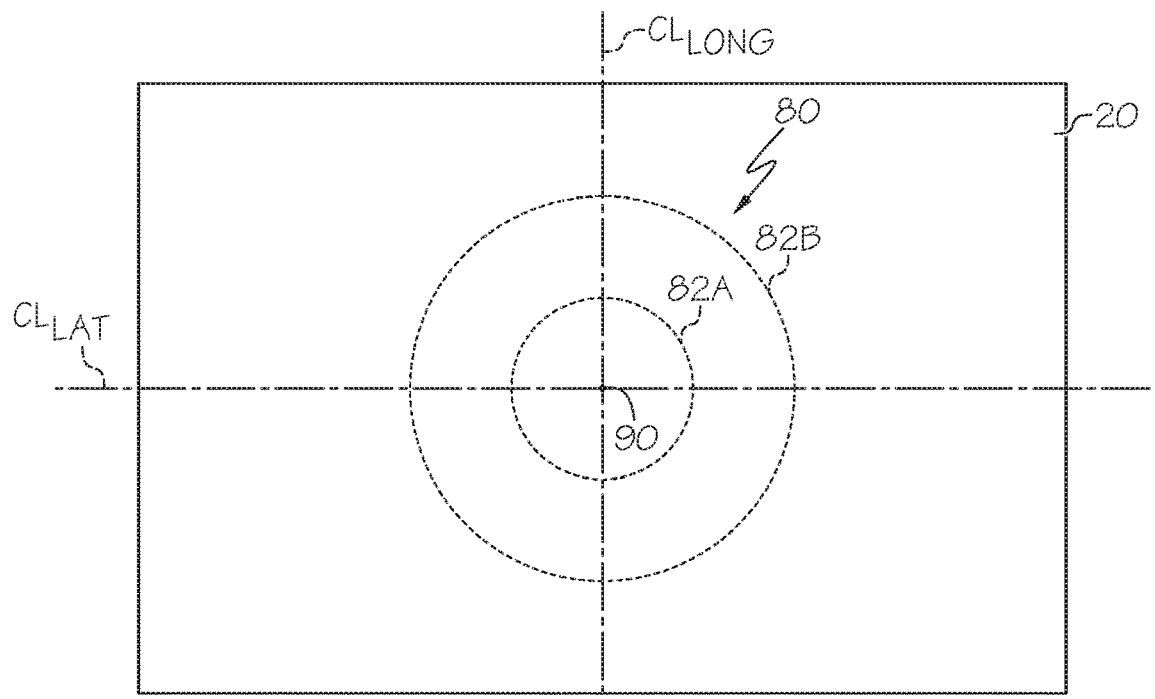
FIG. 8 is a schematic plan view of the patient side of an incontinence pad illustrating a variation of the concept of a "closed figure"

Continuing to refer to FIG. 1, each mark (circles 82A, 82B, 82C) is a closed figure. Referring to FIG. 5, a figure is considered to be a closed figure even if, like circle 82C, it is large enough that a portion or portions of its outline extend past the edge of the article. Such a figure may also be referred to as a virtual closed figure. According to another viewpoint the circular arcs of FIG. 82C, in combination with the intervening linear border segments 104, can be considered to define a closed figure. Referring to FIG. 6, a figure is considered to be a closed figure even if its outline is interrupted, for example in order to include volume labels 92. Referring to FIGS. 7 and 8 a figure is considered to be a closed figure even if its outline is formed by a series of unconnected elements such as dashes (FIG. 7) or dots (FIG. 8).

Figure 9:
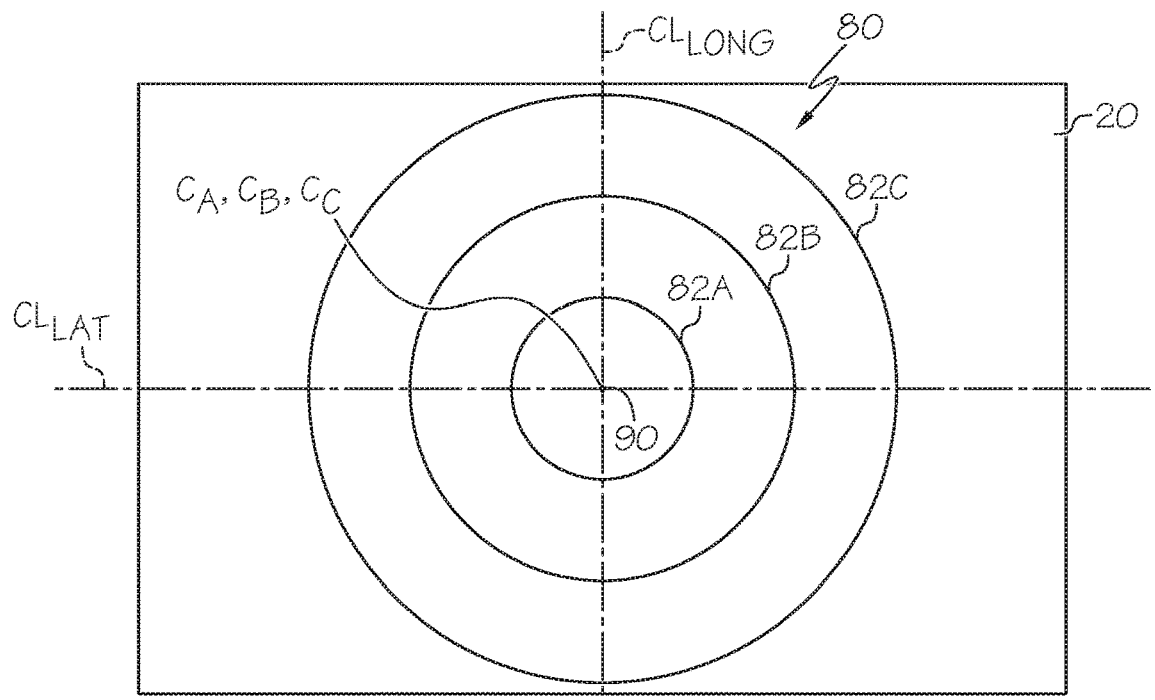
FIG. 9 is a schematic plan view of an embodiment of a pad showing marking clusters comprised of at least one mark whose location on the pad is calibrated to correspond to a particular quantity of liquid having been deposited on the pad at a liquid receiving site thereof and having wicked toward the mark, the marks being in the form of closed figures either centered on a datum of the liquid receiving site or spaced from the datum.

FIG. 9 shows an example, like that of FIG. 1, in which the marking cluster is a set of two or more circles (three in the example). Each circle has a reference point such as its center $C_A$, $C_B$, $C_C$ and a diameter which differs from the diameter of each of the other circles. That is, the circles are differently sized. The circles circumscribe datum 90, and the centers of all the circles lie on the datum.

Figure 10:
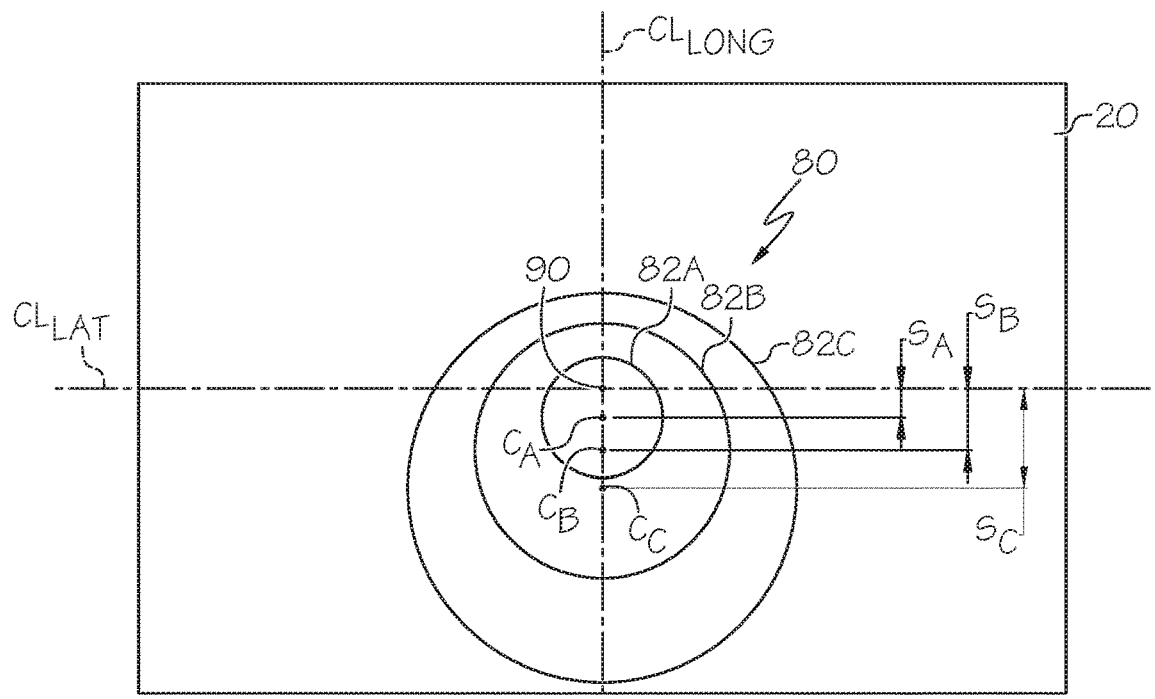
FIG. 10 is a schematic plan view of an embodiment of a pad showing marking clusters comprised of at least one mark whose location on the pad is calibrated to correspond to a particular quantity of liquid having been deposited on the pad at a liquid receiving site thereof and having wicked toward the mark, the marks being in the form of closed figures either centered on a datum of the liquid receiving site or spaced from the datum.

FIG. 10 shows an embodiment similar to that of FIG. 9 in which the circles are once again differently sized and circumscribe datum 90. However the centers of the circles are progressively spaced from the datum in the longitudinal direction by a spacing S which increases with increasing circle diameter. The relationship between S and circle diameter may be linear or nonlinear. The arrangement of FIG. 9 is a limit case in which $S_A=S_B=S_C \ldots =S_n=0$. The offset of FIG. 10 is in the footward direction, however an offset in another direction (e.g. headwardly or laterally) may also be satisfactory.

Figure 11:
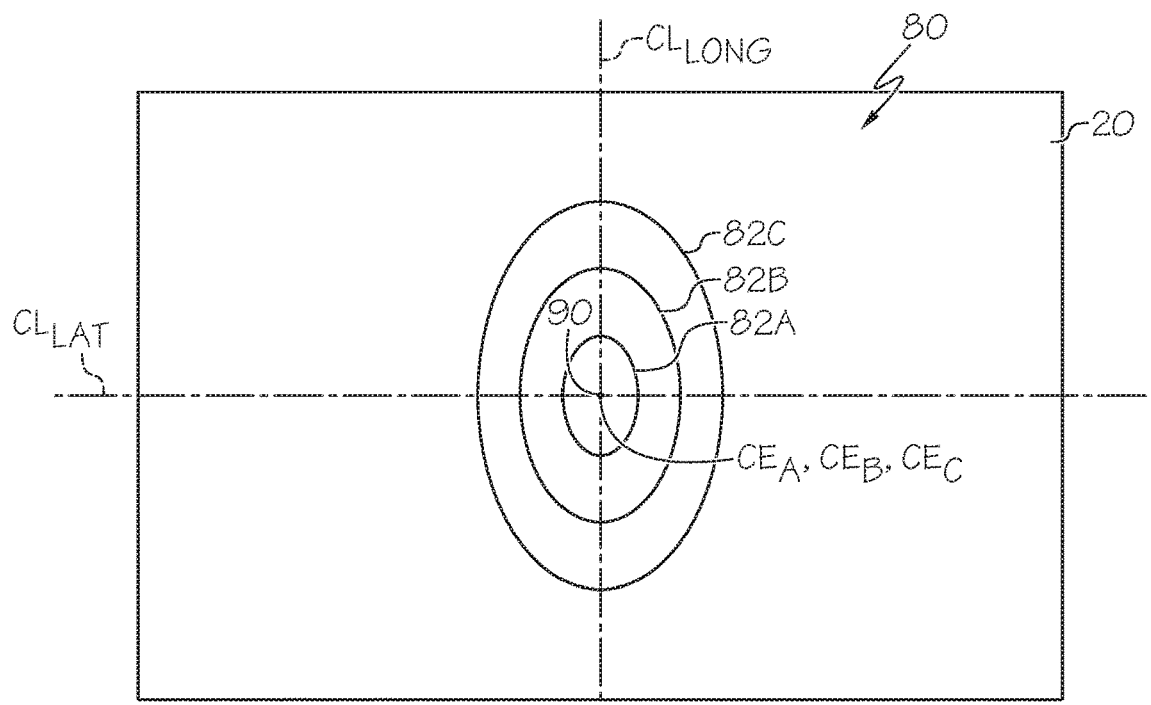
FIG. 11 is a schematic plan view of an embodiment of a pad showing marking clusters comprised of at least one mark whose location on the pad is calibrated to correspond to a particular quantity of liquid having been deposited on the pad at a liquid receiving site thereof and having wicked toward the mark, the marks being in the form of closed figures either centered on a datum of the liquid receiving site or spaced from the datum.
Figure 12:
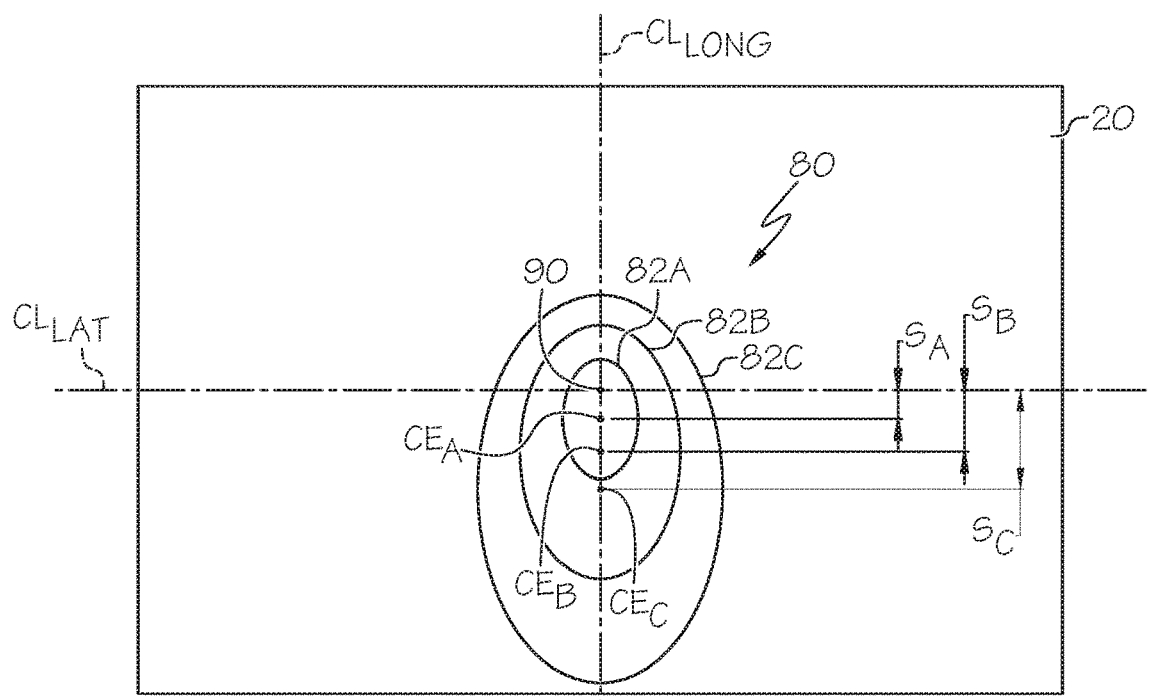
FIG. 12 is a schematic plan view of an embodiment of a pad showing marking clusters comprised of at least one mark whose location on the pad is calibrated to correspond to a particular quantity of liquid having been deposited on the pad at a liquid receiving site thereof and having wicked toward the mark, the marks being in the form of closed figures either centered on a datum of the liquid receiving site or spaced from the datum.
Figure 13:
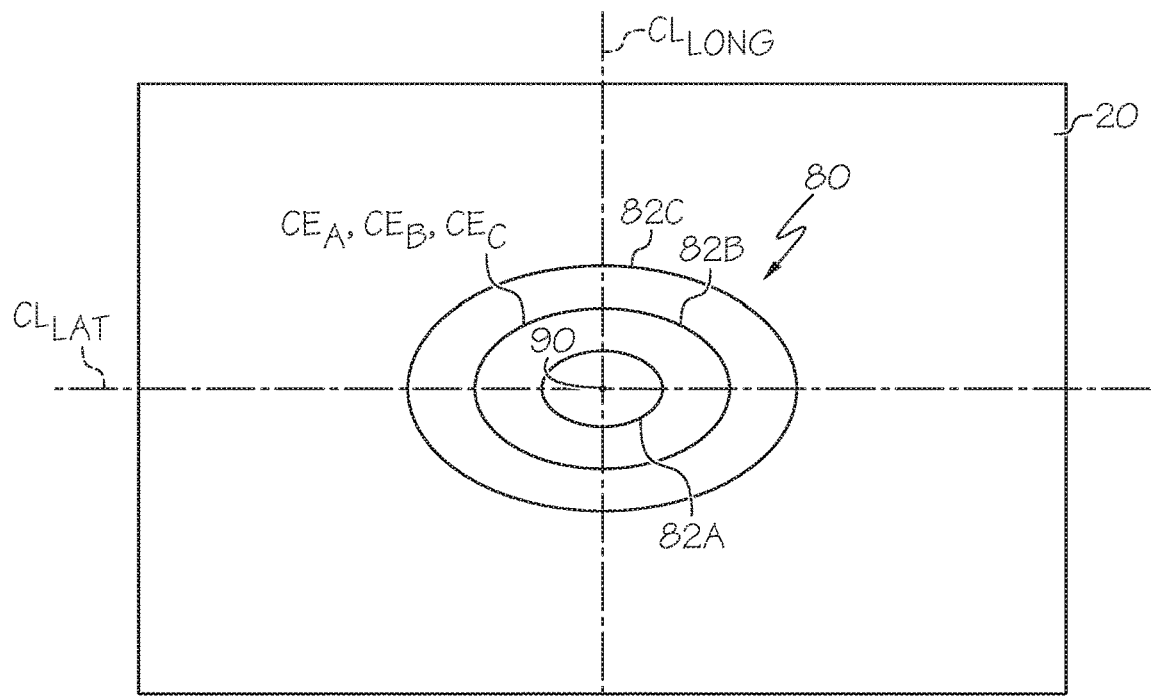
FIG. 13 is a schematic plan view of an embodiment of a pad showing marking clusters comprised of at least one mark whose location on the pad is calibrated to correspond to a particular quantity of liquid having been deposited on the pad at a liquid receiving site thereof and having wicked toward the mark, the marks being in the form of closed figures either centered on a datum of the liquid receiving site or spaced from the datum.
Figure 14:
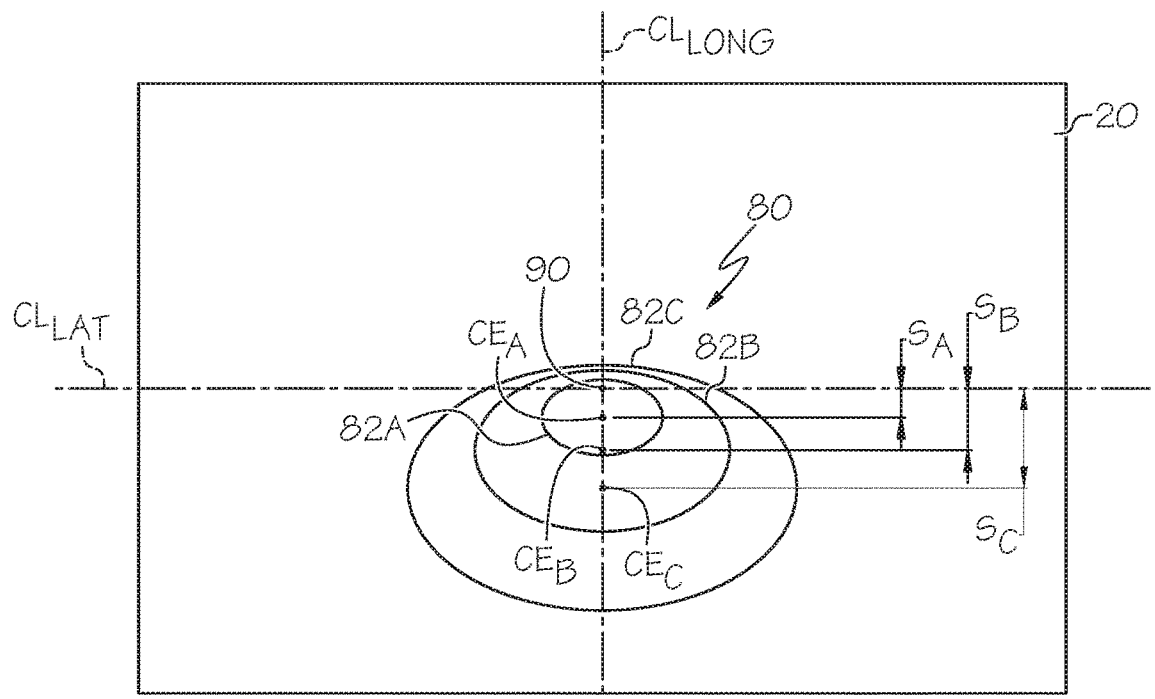
FIG. 14 is a schematic plan view of an embodiment of a pad showing marking clusters comprised of at least one mark whose location on the pad is calibrated to correspond to a particular quantity of liquid having been deposited on the pad at a liquid receiving site thereof and having wicked toward the mark, the marks being in the form of closed figures either centered on a datum of the liquid receiving site or spaced from the datum.

FIGS. 11 and 12 are similar to FIGS. 9 and 10 but show the S=0 limit case and a S≠0 example for elliptical figures whose major axes extend longitudinally. The reference point of each ellipse is taken to be its center CE. An illustration for an oval would be similar. An oval is a figure resembling a squashed circle but, unlike the ellipse, without a precise mathematical definition. Ovals sometimes have only a single axis of reflection symmetry (instead of two). FIGS. 13 and 14 are similar to FIGS. 11 and 12 but show the S=0 limit case and a S≠0 example for elliptical figures whose major axis extends laterally. The reference point of each ellipse is taken to be its center CE. An illustration for an oval would be similar.

Figure 15:
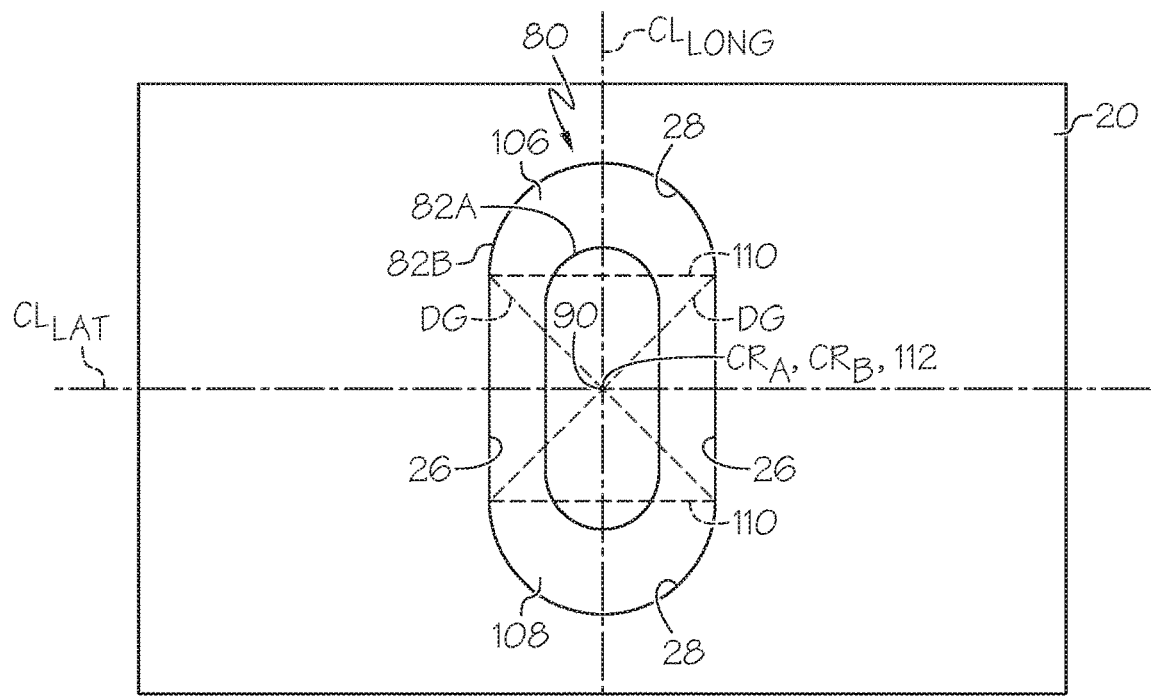
FIG. 15 is a schematic plan view of an embodiment of a pad showing marking clusters comprised of at least one mark whose location on the pad is calibrated to correspond to a particular quantity of liquid having been deposited on the pad at a liquid receiving site thereof and having wicked toward the mark, the marks being in the form of closed figures either centered on a datum of the liquid receiving site or spaced from the datum.
Figure 16:
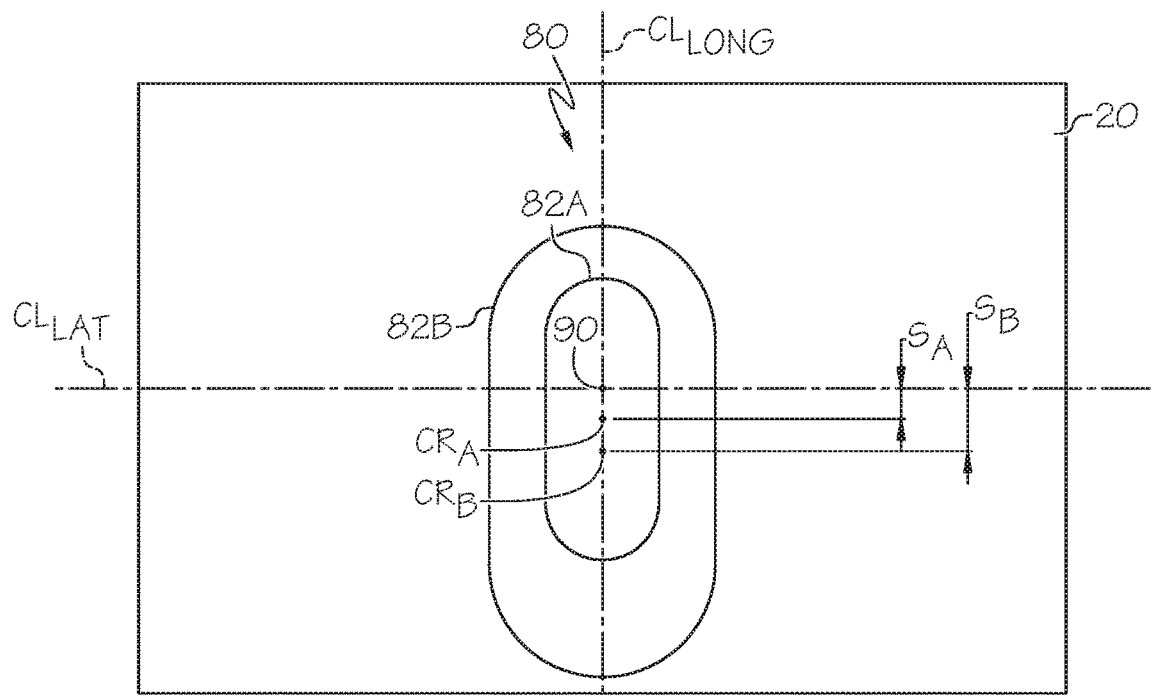
FIG. 16 is a schematic plan view of an embodiment of a pad showing marking clusters comprised of at least one mark whose location on the pad is calibrated to correspond to a particular quantity of liquid having been deposited on the pad at a liquid receiving site thereof and having wicked toward the mark, the marks being in the form of closed figures either centered on a datum of the liquid receiving site or spaced from the datum.
Figure 17:
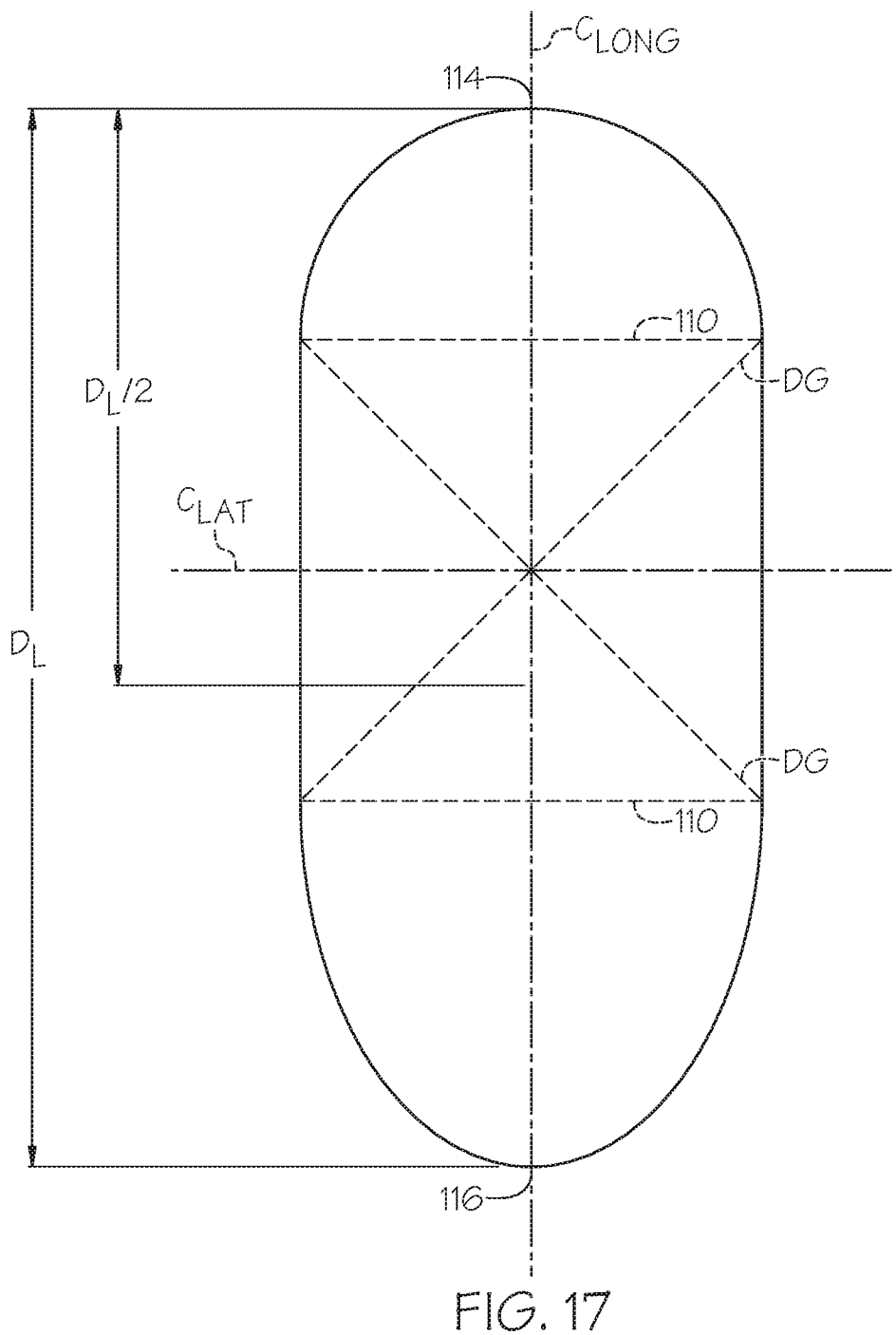
FIG. 17 is a schematic plan view of the pad showing two possible definitions of "center" for a racetrack shaped mark having head and foot ends which are non-congruent.

FIGS. 15 and 16 are similar to FIGS. 11 and 12 but show the S=0 limit case and a S≠0 example for racetrack shaped figures whose major axis extends longitudinally. A racetrack has two parallel straight line segments 26 whose neighboring ends are connected to each other by a curved line 28 which is concave from the vantage point of an observer within the border of the racetrack. Each racetrack has a head end portion 106 and a foot end portion 108 defined by curved line 28 and chord line 110 joining the ends of the curve. The reference point of each racetrack is taken to be its center CR. If the head and foot end portions 106, 108 of the racetrack are congruent as in FIGS. 15, 16 the center CR of the racetrack is the intersection 112 of the diagonals DG of the rectangular portion. If the end portions are not congruent (FIG. 17) the same definition may be used, or some alternate definition of center may be appropriate. One example alternative is the intersection of the lateral and longitudinal centerlines $CL_{LAT}$, $CL_{LONG}$ where $CL_{LAT}$ is midway between the head end and foot end extremities 114, 116 of the pad.

Although FIGS. 8, 10, 12, 14, and 16 show nonzero longitudinal spacing S of the nonconcentric closed figures, lateral spacing may be used instead of or in addition to longitudinal spacing.

Figure 18:
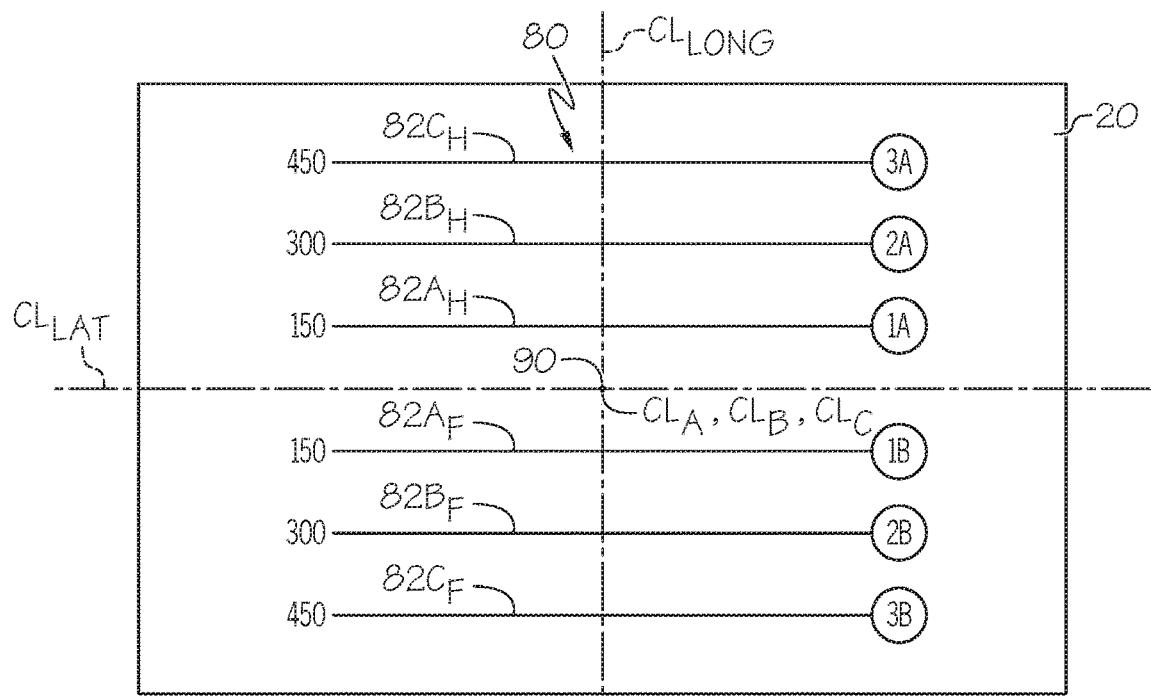
FIG. 18 is a schematic plan view of the patient side of an incontinence pad showing embodiments in which the marks of the marking clusters are various arrangements of straight lines.

FIG. 18 shows an example in which the mark or marks 82 of the marking cluster 80 is a set of one or more lines (three in the example) which do not define an actual or virtual closed figure. Each line is displaced longitudinally from datum 90. Subscripts H and F are used to indicate whether a line is headwardly or footwardly of datum 90. Each line which is footwardly of the datum has a companion which is headwardly of the datum, and the companions are equally spaced from the datum (and therefore from lateral centerline $CL_{LAT}$) in opposite directions. This may be referred to as a symmetrical spacing or distribution, and is analogous to the concentric closed figures of FIGS. 9, 11, 13, 15. In other words, each line on the headward side of the datum has an ordinality indicated by a circled numeral (1A, 2A, 3A, . . . ), each line on the footward side of the datum has an ordinality (1B, 2B, 3B . . . ), and lines of numerically equal ordinality on opposite sides of the datum are equally spaced from the datum in the longitudinal direction. By way of further analogy with the closed figures, the "center" $CL_A$, $CL_B$, $CL_C$ of a pair of lines of equal ordinality can be considered to be the point on centerline $CL_{LONG}$ which is longitudinally midway between the lines of the pair. In view of the symmetry, $CL_A$, $CL_B$, $CL_C$ all lie on datum 90.

Figure 19:
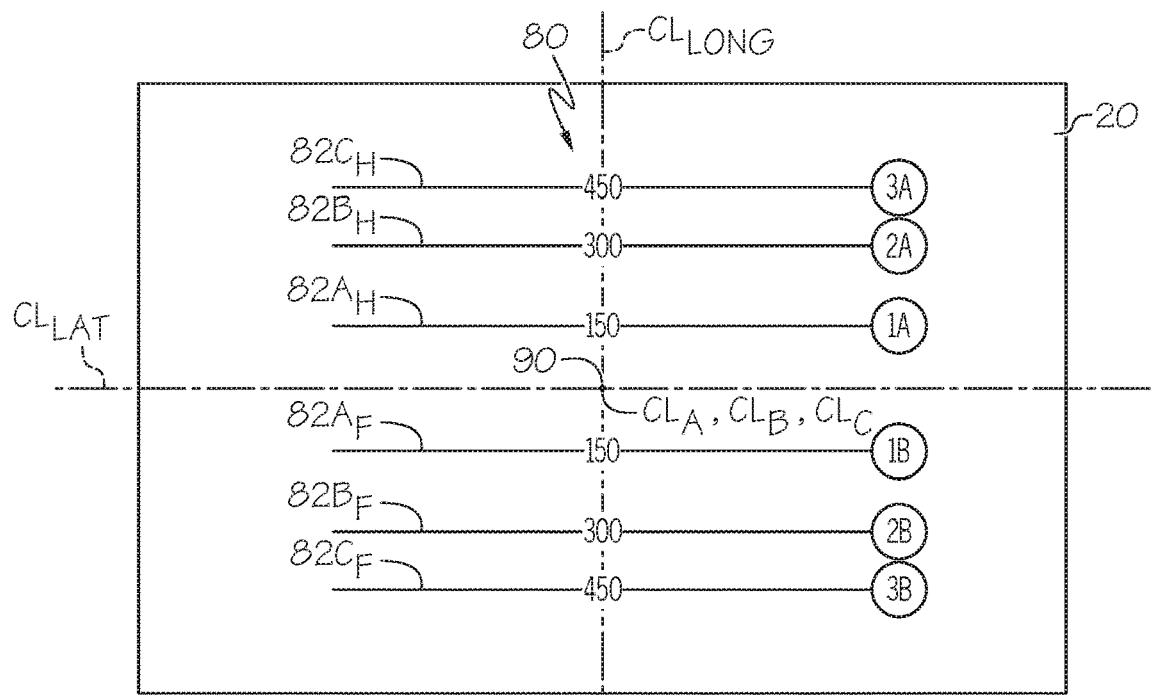
FIG. 19 is a schematic plan view of the patient side of an incontinence pad showing embodiments in which the marks of the marking clusters are various arrangements of straight lines.

FIG. 19 shows an embodiment in which the lines on each side (headward or footward) of the datum are not equally spaced from each other. In another embodiment, not illustrated, not all lines on one side of the datum have a companion on the other side of the datum. The lines are shown as extending only partially across the width of the pad, however the lines could instead be full width lines spanning the entire distance between the left and right edges of the pad. In the non-closed figure embodiments one or more lines on the same side (headward or footward) of the datum may be considered to be a cluster, and one or more lines on the other side of the datum, if such line or lines are present, may be considered to be a different cluster. Alternatively, one or more pairs of lines, one member of the pair on one side of the datum and the other member of the pair on the other side of the datum, may be considered to be a cluster, in which case each line of any given pair, standing alone, may be considered to be an individual mark of the marking cluster. Alternatively, the two lines of the pair, taken together, may be considered to be a single mark of the marking cluster.

Figure 20:
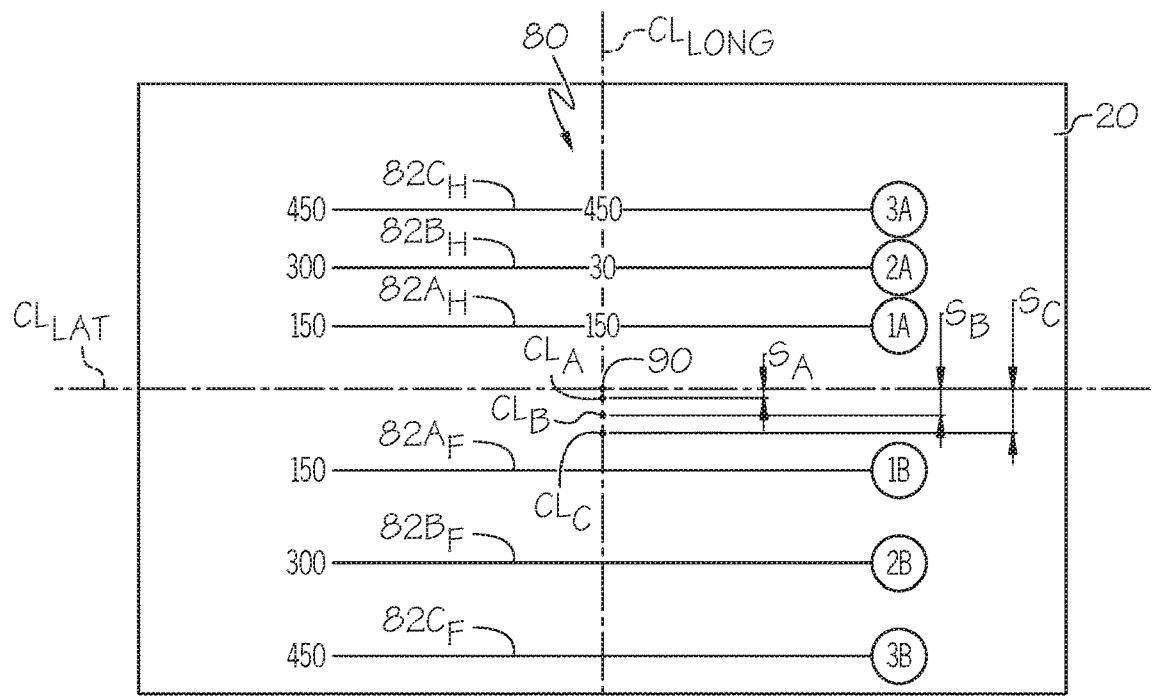
FIG. 20 is a schematic plan view of the patient side of an incontinence pad showing embodiments in which the marks of the marking clusters are various arrangements of straight lines.

FIG. 20 shows a nonsymmetrical straight line embodiment. The inter-line spacing on the headward side of the datum is smaller than the inter-line spacing on the footward side of the datum. This is analogous to the non-concentric closed figures of FIGS. 10, 12, 14, 16. Using the notion that the "center" of a pair of lines of equal ordinality is the point on centerline $CL_{LONG}$ which is longitudinally midway between those lines, centers $CL_A$, $CL_B$, $CL_C$ are spaced from datum 90 by nonzero amounts $S_A$, $S_B$, $S_C$. As with the closed figure analogues, the symmetrical distributions of FIGS. 18-19 can be considered to be S=0 limit cases of FIG. 20.

Figure 21:
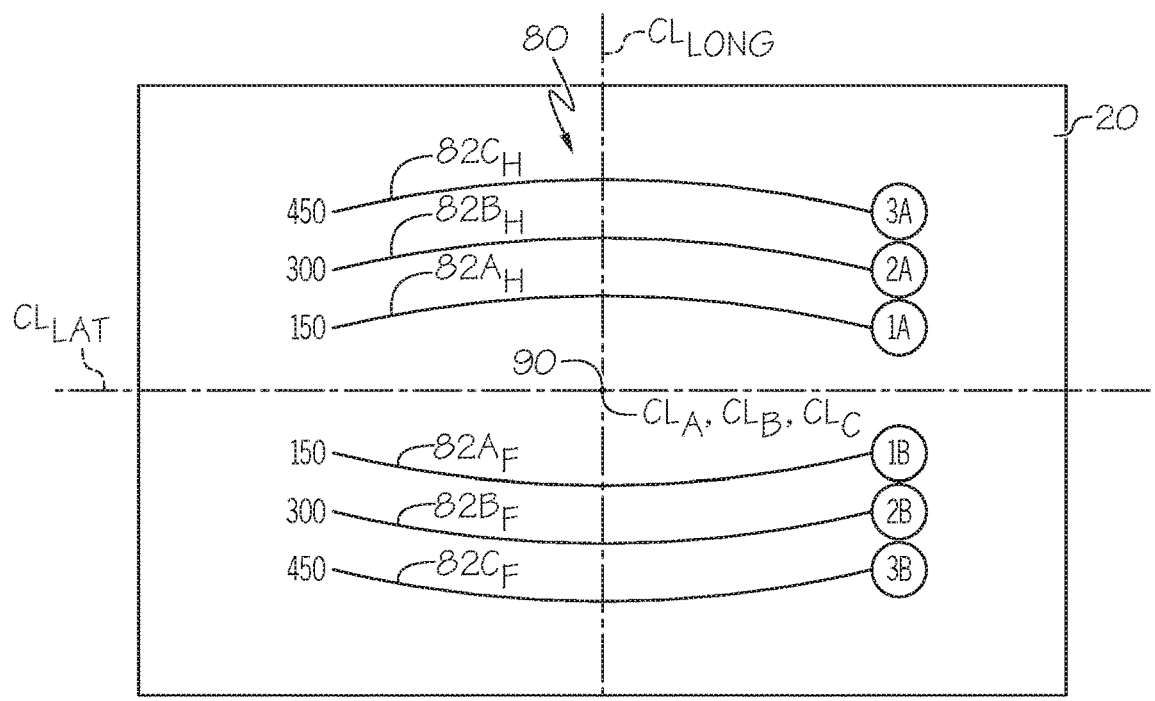
FIG. 21 is a schematic plan view of an embodiment of the pad in which the marks are curved lines.

FIG. 21 shows a variant in which the lines are curved rather than straight. The particular example is a symmetrical distribution in the lateral direction. The variations described above in connection with straight line apply to curved line embodiments.

Figure 22:
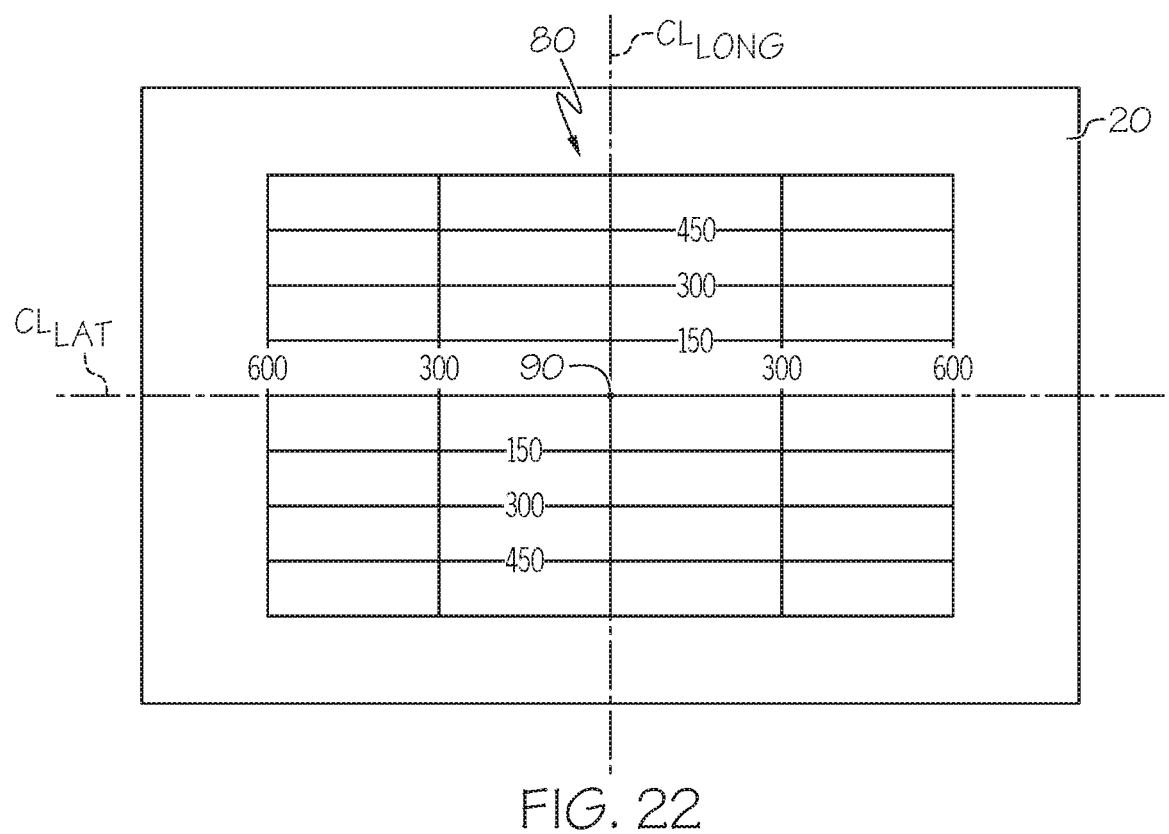
FIG. 22 is a schematic plan view of an embodiment of the pad in which the marks are laterally and longitudinally extending straight lines which define a grid.

Although FIGS. 18-21 show longitudinally spaced lines, laterally spaced line may be used instead of or in addition to longitudinal spaced lines. FIG. 22 shows an example of a grid formed of laterally and longitudinally extending straight lines. The laterally extending lines are distributed symmetrically relative to the laterally extending centerline $CL_{LAT}$, and the longitudinally extending lines are distributed symmetrically relative to the longitudinally extending centerline $CL_{LONG}$. Nonsymmetrical spacing may also be used.

In general, the marking cluster is a set of one or more marks, each of which is a differently sized figure of the same geometric class (e.g. circle, ellipse, oval, rectangle, racetrack, straight line, curved line). In the case of a single mark cluster, the notion of differently sized does not apply. In the case of a closed figure, a test for "differently sized" may be simply a difference in the lengths of their perimeters, a figure with a longer perimeter being of a larger size than a figure with a smaller perimeter. In the case of a line, as opposed to a closed figure, a test of "differently sized" may be the separation of two lines of equal ordinality, larger separation corresponding to larger size and smaller separation corresponding to smaller size. Each mark of a cluster has a location on the article which is calibrated to correspond to a particular quantity of liquid having been deposited on the article at the liquid receiving site and having been wicked toward the mark. Alternatively each mark of a cluster may be thought of as being spaced from a datum of the pad by a spacing calibrated to correspond to a particular quantity of liquid having been deposited on the article at the liquid receiving site and having been wicked toward the mark. In the case of a mark or marks in the form of a closed figure, each closed figure circumscribes a datum 90 of the liquid receiving site. The closed figures are distributed on the article with reference points (e.g. centers) of the figures longitudinally spaced headwardly or footwardly from the liquid receiving site datum and/or laterally leftwardly or rightwardly spaced from the datum. At the lower limit, the spacing may be zero. In the case of a mark or marks in the form of a line straight or curved lines of equal ordinality are on opposite sides of the datum. The lines are distributed on the article with reference points (e.g. "centers") of lines of equal ordinality longitudinally spaced headwardly or footwardly from the liquid receiving site datum and/or laterally leftwardly or rightwardly spaced from the datum. In the limit, the spacing may be zero.

In the somewhat less general case in which the marking cluster is a set of one or more closed figures, each closed figure is a differently sized figure of the same geometric class (e.g. circle, ellipse, oval, rectangle, racetrack). In the case of a single mark cluster, the notion of "differently sized" does not apply. Each mark of a cluster has a location on the article which is calibrated to correspond to a particular quantity of liquid having been deposited on the article at the liquid receiving site and having been wicked toward the mark. Alternatively each mark of a cluster may be thought of as being spaced from a datum of the pad by a spacing calibrated to correspond to a particular quantity of liquid having been deposited on the article at the liquid receiving site and having been wicked toward the mark. Each closed figure circumscribes a datum 90 of the liquid receiving site. The closed figures are distributed on the article with reference points (e.g. centers) of the figures longitudinally spaced headwardly or footwardly from the liquid receiving site datum and/or laterally leftwardly or rightwardly spaced from the datum. In the limit, the spacing may be zero.

In another somewhat less general case in which the marking cluster is a line, each line is a non-closed figure of the same geometric class (e.g. straight line, curved line). Each mark of a cluster has a location on the article which is calibrated to correspond to a particular quantity of liquid having been deposited on the article at the liquid receiving site and having been wicked toward the mark. Alternatively, each mark of a cluster may be thought of as being spaced from a datum of the pad by a spacing calibrated to correspond to a particular quantity of liquid having been deposited on the article at the liquid receiving site and having been wicked toward the mark. Lines of equal ordinality are on opposite sides of the datum. The lines are distributed on the article with reference points (e.g. "centers") of lines of equal ordinality longitudinally spaced headwardly or footwardly from the liquid receiving site datum and/or laterally leftwardly or rightwardly spaced from the datum. In the limit, the spacing may be zero.

Figure 23:
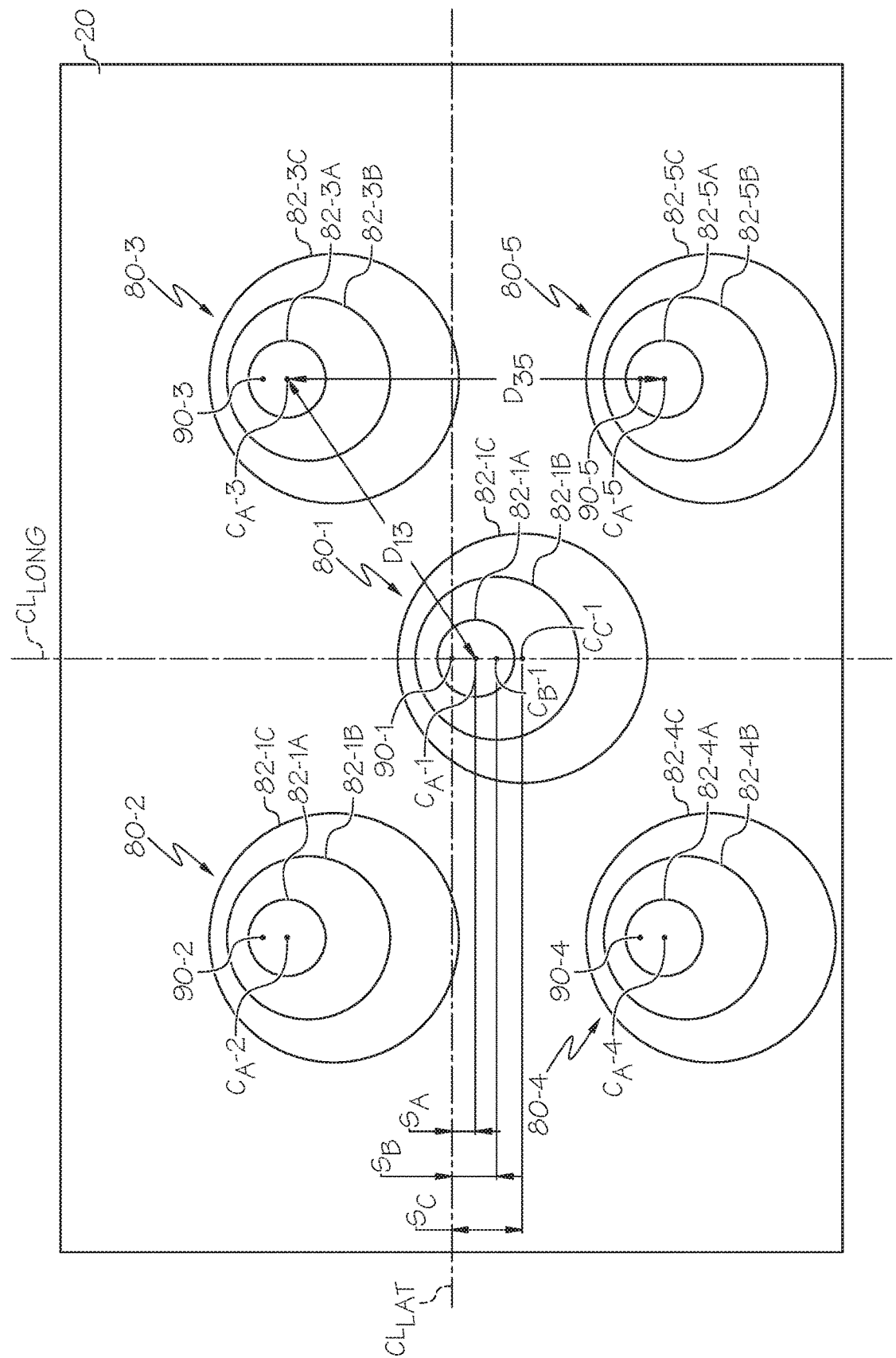
FIG. 23 is a schematic plan view of an embodiment of the pad having multiple marking clusters which are disjoint.

FIG. 23 shows another embodiment of the article in the form of an incontinence pad. In the embodiment of FIG. 23 marking cluster 80-1 is a first marking cluster hence the "−1" suffix. The first marking cluster is a set of circles whose centers are spaced from datum 90-1. This is similar to the arrangement of FIG. 10, however other geometries can be used, including the various closed and non-closed (line) geometries disclosed above.

The pad includes one or more auxiliary marking clusters 80-2, 80-3, 80-4, 80-5. The auxiliary marking clusters account for the possibility that the pad may not have been properly positioned under the patient, i.e. that that the actual site at which urine deposition occurs may not be approximately the liquid receiving site envisioned by the designer. Another possibility is that the patient moved relative to a properly positioned pad. Each marking cluster in the example of FIG. 23 includes three circular figures, and each circle is spaced from its datum by a nonzero spacing S.

Each auxiliary marking cluster is offset from the first marking cluster and from the other marking clusters. For example the offset between marking cluster 80-1 and marking cluster 80-3 is $O_{13}$, the distance between the centers of the innermost circles of marking clusters 80-1 and 80-3. Similarly the offset between marking cluster 80-3 and marking cluster 80-5 is $O_{35}$, the distance between the centers of the innermost circles of marking clusters 80-3 and 80-5. Each marking cluster includes at least one mark 82 whose location on the article is calibrated to correspond to a particular amount of liquid having been deposited on the article at an auxiliary liquid receiving site associated with the cluster (datums 90-1 through 90-5) and having wicked toward the mark. Reference numerals 82 are applied only to the marks of marking cluster 80-4 to avoid undue clutter on the drawing.

In the pad of FIG. 23, each auxiliary marking cluster is disjoint from the first marking cluster and from each of the other auxiliary marking clusters. Disjoint means that the outermost figure of any cluster does not overlap the outermost figure of any other cluster.

Figure 24:
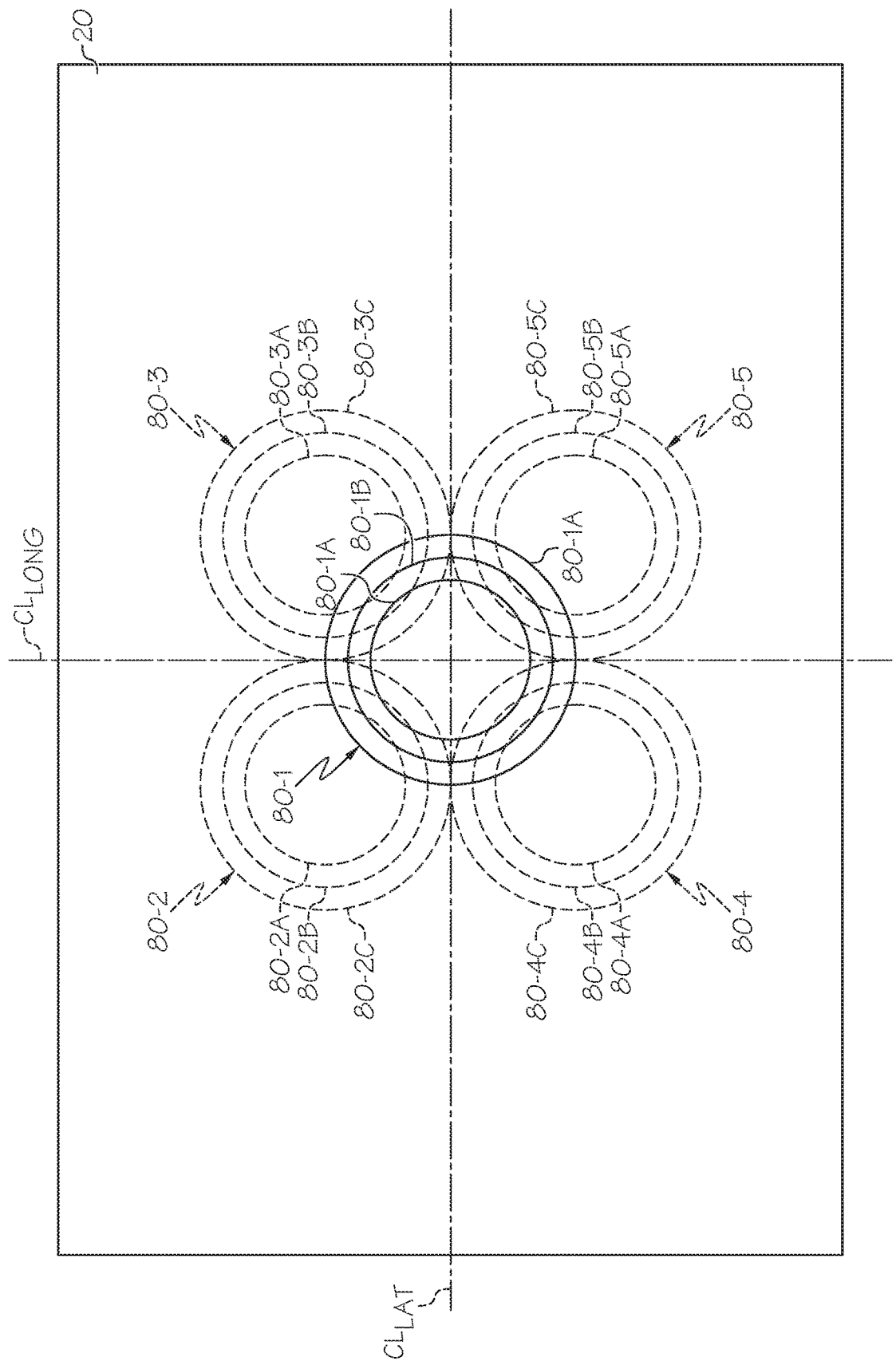
FIG. 24 is a schematic plan view of an embodiment of the pad having multiple marking clusters which are overlapping.

FIG. 24 shows an embodiment where the clusters are not disjoint. Each cluster is comprised of a set of three concentric circles so that spacing S of the figures of each cluster relative to its datum is zero. The marks of the auxiliary clusters have a different form than those of the first cluster (e.g. dashed vs. solid) to help the user of the pad distinguish between the first cluster and the auxiliary clusters, especially where they overlap.

Although not depicted in FIGS. 23-24, a label may be associated with at least one mark of the first cluster and/or with at least one mark of at least one auxiliary cluster to indicate the particular amount of liquid deposited at the liquid receiving site associated with the cluster.

The incontinence pad described above is useful for determining the volume of an incontinence episode without catheterization in situations where catheterization is not required for other reasons. The above describe RFID subsystem (tag, traces, reader) are superfluous for the purpose of measuring urine output. However the pad may include the RFID subsystem in addition to the above described liquid measurement features.

Although this disclosure refers to specific embodiments, it will be understood by those skilled in the art that various changes in form and detail may be made without departing from the subject matter set forth in the accompanying claims.

We claim:

1. A liquid measurement article comprising:
 a liquid permeable layer, an absorbent wicking layer, and a liquid impermeable layer, wherein the absorbent wicking layer is disposed between the liquid permeable layer and the liquid impermeable layer;
 a marking cluster on the liquid permeable layer, the marking cluster having at least one mark whose location on the article is calibrated to correspond to a particular quantity of liquid having been deposited on the article at a liquid receiving site thereof and having wicked toward the at least one mark; and
 a label associated with at least one of the at least one mark to indicate the particular quantity of liquid.

2. The article of claim 1 wherein the label is a volume label.

3. The article of claim 1 wherein the absorbent wicking layer has a radially uniform wicking response.

4. The article of claim 1 wherein the article is a sheet.

5. The article of claim 1 wherein the article is planar.

6. The article of claim 1 wherein the article is nonwearable.

7. The article of claim 1 wherein the article has a planform which is not adapted to conform to a human surface anatomy feature.

8. The article of claim 1 wherein the article is not adapted to conform to a human crotch.

9. The article of claim 1 wherein the at least one mark comprises two or more marks.

10. The article of claim 1 wherein the at least one mark is a closed figure.

11. The article of claim 10 wherein the closed figure is centered on a datum representing the liquid receiving site.

12. The article of claim 11 wherein closed figures are concentric circles circumscribing the liquid receiving site.

13. The article of claim 1 wherein the article does not chemically react with urine to change color.

14. The article of claim 1 wherein the marking cluster is a set of two or more marks, each of which is a differently sized closed figure of the same geometric class, each closed figure circumscribing a datum of the liquid receiving site, each closed figure being arranged on the article with reference points of each closed figure longitudinally and/or laterally spaced from the datum by a spacing.

15. The article of claim 14 wherein the spacing is zero.

16. The article of claim 1 wherein the marking cluster is a set of two or more lines.

17. The article of claim 16 wherein the lines are straight lines.

18. The article of claim 1 wherein the article is a pad having:
 an RFID tag and an associated electrical trace assembly which defines an open circuit;
 wherein the absorbent wicking layer and barrier layer are adapted to promote closure of the open circuit in response to deposition of a threshold amount of liquid thereon.

19. The article of claim 1 wherein the marking cluster is a first marking cluster and the article includes:
 one or more auxiliary marking clusters each of which:
  A) is offset from the first marking cluster and from each other,
  B) has at least one mark whose location on the article is calibrated to correspond to a particular amount of liquid having been deposited on the article at an auxiliary liquid receiving site associated with the one or more auxiliary marking clusters and having wicked toward the at least one mark.

20. The article of claim 19 wherein each of the one or more auxiliary marking clusters is disjoint from the first marking cluster and from each other auxiliary marking clusters.

21. The article of claim 19 including an auxiliary label associated with at least one mark of the at least one auxiliary marking cluster to indicate the particular amount of liquid deposited at the liquid receiving site associated with the at least one auxiliary marking cluster.

22. The article of claim 1 having a person side and a bottom side, the article comprised of layers ordered as set forth below proceeding from the person side to the bottom side:
 the liquid permeable layer;
 the absorbent wicking layer;
 the liquid impermeable layer; and
 a strengthening layer.

23. The article of claim 22 wherein the liquid impermeable layer and the strengthening layer are sublayers of a back sheet, and wherein the back sheet includes an electrical trace assembly which defines an open circuit, and the article includes a barrier layer between the absorbent wicking layer and the back sheet, the barrier layer adapted to regulate liquid migration from the absorbent wicking layer to the back sheet.

24. The article of claim 1 wherein the marking cluster is a set of one or more closed figures, each closed figure being a differently sized closed figure of the same geometric class, each closed figure having a location on the cluster which is calibrated to correspond to the particular quantity of liquid having been deposited on the article at the liquid receiving site and having been wicked toward the closed figure.

25. The article of claim 1 wherein the marking cluster is a set of one or more lines, each line of a cluster being spaced from a datum representative of the liquid receiving site by a spacing calibrated to correspond to a particular quantity of liquid having been deposited on the article at the liquid receiving site and having been wicked toward the line.

26. A liquid measurement article comprising:
- a liquid permeable layer, an absorbent wicking layer, and a liquid impermeable layer, wherein the absorbent wicking layer is disposed between the liquid permeable layer and the liquid impermeable layer;
- at least one mark on the liquid permeable layer, the at least one mark being spaced from a liquid receiving site datum of the article by a spacing calibrated to correspond to a particular quantity of liquid having been deposited on the article at the liquid receiving site datum and having been wicked toward the at least one mark; and
- a label associated with at least one of the at least one mark to indicate the particular quantity of liquid.

\* \* \* \* \*